United States Patent [19]

Draenert

[11] 4,373,217
[45] Feb. 15, 1983

[54] IMPLANTATION MATERIALS AND A PROCESS FOR THE PRODUCTION THEREOF

[75] Inventor: Klaus Draenert, Ottobrunn, Fed. Rep. of Germany

[73] Assignee: Merck Patent Gesellschaft mit Beschränkter Haftung, Darmstadt, Fed. Rep. of Germany

[21] Appl. No.: 121,772

[22] Filed: Feb. 15, 1980

[30] Foreign Application Priority Data

Feb. 16, 1979 [DE] Fed. Rep. of Germany ....... 2905878

[51] Int. Cl.$^3$ .......................... A61F 1/00; C08L 3/08; C08L 3/10; C08K 3/32
[52] U.S. Cl. ....................................... 3/1.9; 128/92 B; 128/92 G; 433/201; 523/114; 523/115; 523/116
[58] Field of Search ........... 433/201; 128/92 B, 92 G; 260/42.52, 42.53; 523/116, 115, 114; 3/1.9

[56] References Cited

U.S. PATENT DOCUMENTS

| | | | |
|---|---|---|---|
| 3,609,867 | 10/1971 | Hodosh. | |
| 3,787,900 | 1/1974 | McGee | 433/201 |
| 3,882,858 | 5/1975 | Klemm | 128/92 G |
| 4,059,684 | 11/1977 | Gross et al. | 424/81 |
| 4,093,576 | 6/1978 | de Wijn | 128/92 R |
| 4,113,500 | 9/1978 | Ebihara et al. | 433/201 |
| 4,141,864 | 2/1979 | Rijke et al. | 260/42.53 |
| 4,191,740 | 3/1980 | Heusser et al. | 128/92 B |

FOREIGN PATENT DOCUMENTS

2620890 3/1979 Fed. Rep. of Germany.
1541793 3/1979 United Kingdom.

OTHER PUBLICATIONS

Chem. Abstracts 81: 29549u (1974).
Chem. Abstracts 82: 103178m (1975).
Chem. Abstracts 86: 47297t (1977).
J. Biomed. Mater. Res. 11: 373-394 by Rijke et al.
"Antibiotik-Fibel", 4th Ed., (1975), bottom of p. 373 to top of p. 374.

*Primary Examiner*—Allan Lieberman
*Attorney, Agent, or Firm*—Millen & White

[57] ABSTRACT

An implantation material comprises a polymeric base of an acrylate, a polymethacrylate, a copolymer of an acrylate and a methacrylate or a mixture thereof, and 5-35% by weight of resorbable tricalcium phosphate of a particle size of 50-300 $\mu$m, and an available pore volume of less than 0.1 ml/g.

17 Claims, No Drawings

IMPLANTATION MATERIALS AND A PROCESS FOR THE PRODUCTION THEREOF

BACKGROUND OF THE INVENTION

The present invention relates to implantation materials based on polymeric acrylates, especially polymethyl methacrylate, which can be utilized, in particular, as bone replacement, bone bonding and prosthesis anchoring materials.

These implantation materials, also known as bone cements, are not resorbed by the body but rather are enveloped by the body's own tissue after growing into place. A stable bond of implant/body is established only if the implant grows into place in an "osseous" fashion, i.e., bone tissue extends into the direct vicinity of the implant surface. However, there frequently occurs a biomechanical overstressing of the implant, i.e., due to bending and shear forces acting on the implant, which forces must be absorbed by the relatively small boundary surface area of implant/body. Due to this overstressing, reconstruction zones are formed with reticular ossifications and also a taut layer of connective tissue is formed instead of bone tissue. This leads to a loosening of the implant.

A great number of attempts has been made to ameliorate this condition by enlarging the implant/body interface, for example, by providing the implant with a porous structure permitting the implant to be permeated throughout by a growth of body tissue. Thus, DOS [German Unexamined Laid-Open Application] No. 2,008,708 proposes, especially for tooth implants, to add to the acrylic polymer, in addition to ground root substance of natural teeth and optionally a blowing agent, up to 30% by weight of ground "inorganic bone". By the dissolution of the inorganic bone in the body, a high porosity is to be established which is to promote a solid bond with the adjoining tissue.

DOS No. 2,620,890 suggests addition to the polymer of calcium phosphate in a quantitative ratio of 1:1 to 5:1, corresponding to a calcium phosphate proportion of 50–83%. Calcium phosphate is likewise disintegrated and resorbed in the body so that again a very high porosity is obtained which is to promote a durable bond of implant/body by the subsequent growth of body tissue. The same principle is also utilized in the prosthesis anchoring device described in DOS No. 2,620,907, wherein calcium phosphate particles having a diameter of 0.5–1 mm are applied as a dense packing of spheres so that, after the resorption of the calcium phosphate, a continuous pore system is to be produced which can be filled in by body tissue.

Also, DOS No. 2,518,153 describes a process wherein, by admixing an aqueous gel with the polymeric mixture, a network of gel filaments is to be provided which can be filled in by bone tissue.

A porosity throughout the cement is also to be achieved in the method described in J. Biomed. Mater. Res. 11: 373–394 (1977) wherein a soluble filler is admixed with the cement. Sucrose is the prime such filler, but calcium phosphate is likewise mentioned as a filler. These investigations have shown that a porosity throughout the cement, with sufficiently large pores, is attained only at a content of soluble additives of at least about 40%, corresponding approximately to the data set forth in DOS's Nos. 2,620,890 and 2,620,907.

However, all of these bone cements lack the required stability. Although it is indicated in J. Biomed. Mater. Res. 11: 373–394 (1977) that even a bone cement with about 40% sucrose additive still exhibits the strength of natural bone, this is true, at best, for a one-time stress. In case of repeated stresses, however, fatigue of the "dead" implant material occurs very quickly, and the material becomes brittle. A sufficient stability would be attained in these implants only if a complete permeative growth had taken place. This, however, would take many months and it is impossible to keep the corresponding limbs at rest for such a long period of time.

SUMMARY OF THE INVENTION

Accordingly, it is an object of this invention to provide a long-needed implantation material having sufficient stability, e.g., to withstand the aforementioned stresses, commencing directly after introduction into the body, and which also ensures a good long-term stability by the ability to form a firm bond with the surrounding bone tissue in a short period of time.

Upon further study of the specification and appended claims, further objects and advantages of this invention will become apparent to those skilled in the art.

The present invention's attainment of these objects is based on the finding that by mixing a special tricalcium phosphate in a specific amount and, above all, in an exactly defined particle size, to the conventional bone cements based on polyacrylates, an implantation material is obtained which meets all requirements with respect to short-term as well as long-term stability.

Accordingly, these objects have been attained by one aspect of this invention by providing an implantation material comprising a base of a polyacrylate or a polymethacrylate and 5–35% by weight of the total mass of resorbable tricalcium phosphate having a particle size of 50 $\mu$m to 300 $\mu$m and an available pore volume of less than 0.1 ml/g.

In other aspects, this invention also relates to the use of resorbable tricalcium phosphate having a particle size of 50 $\mu$m to 300 $\mu$m and an available pore volume of less than 0.1 ml/g as an additive to implantation materials having a polyacrylate base, and to the use of the implantation materials in the combating of bone defects.

Furthermore, in another aspect, this invention relates to a method for preparing implantation materials having a polyacrylate or polymethacrylate base, comprising adding tricalcium phosphate to the monomer, which triggers polymerization, prior to or after the monomer is mixed with the prepolymer, and uniformly mixing the components together.

DETAILED DISCUSSION

Among the special advantages of the implantation materials of this invention is the fact that the bond of the basic acrylate polymer is not negatively affected by the addition of this invention, due to the relatively low amounts of tricalcium phosphate added. In contradistinction to the results of the proposed solution of the above-cited J. Biomed. Meter. Res. reference, for this invention, even an improvement in the compressive load bearing ability of the cured implantation materials is surprisingly observed. In addition, the volume shrinkage normally noticed in the curing of customary bone cements is markedly reduced. Also, the added tricalcium phosphate improves heat removal during the polymerization process, so that the danger of so-called heat necroses is thereby markedly diminished.

Surprisingly, with the implantation materials of this invention, a very firm bond between implant and body tissue is attained even though normally there is not a complete permeative growth of body tissue through the implant. Rather, only the tricalcium phosphate particles located on the surface of the implant are resorbed, so that the thus-produced marginal porosity is filled in by bone tissue. However, due to the particle size of the tricalcium phosphate required by this invention, the pore size of this marginal porosity is controlled in such a way that channels are produced of dimensions which are especially advantageous for bone growth. Only thereby is a primarily osseous filling of the porosities obtained. Due to resorption of the tricalcium phosphate particles in the boundary zone, a significant enlargement of contact area is produced; thereby, the forces acting on the interface are distributed over a larger area.

These channels, as mentioned above, normally extend only over a surface of the implant accessible to body fluid. However, if, accidentally, several tricalcium phosphate particles are adjacent one another, these channels also will extend farther into the interior of the implant. This porosity present on the surface of the implant, which can be rapidly filled in by bone tissue, is sufficient for considerably improving the bond of implant/bone, despite the relatively small amount of 5-35% by weight of tricalcium phosphate employed.

The term "tricalcium phosphate" as used in the present application, is a generic expression which includes a number of various materials essentially defined by the chemical formula $Ca_3(PO_4)_2$, wherein the ratio of Ca:P is approximately 3:2. In addition to the pure tricalcium phosphates, such as, for example $\alpha$- or $\beta$-whitlockite, however, they include also the materials only approximately defined by the formula $Ca_3(PO_4)_2$, such as, for example, apatites or phosphorite. In any event, the tricalcium phosphate is to be resorbable in the body.

These materials are known per se and can be produced according to conventional methods. Essentially, these methods are precipitation or sintering processes, or a combination of such processes. Precipitation and sintering processes for the preparation of the calcium phosphates are described in the standard works of inorganic chemistry, e.g., Gmelin. Suitable starting materials are normally soluble calcium salts and soluble phosphates, or, for the sintering methods, for example, CaO, CaOH, $CACO_3$ and $CaHPO_4$ which are sintered together with $P_2O_5$ or with one another.

The calcium phosphates obtained in the precipitation methods are normally relatively soft and possess a large pore volume on the order of about 0.3-0.5 ml/g. These calcium phosphates have advantages as well as disadvantages. It is advantageous that such relatively porous calcium phosphates are rapidly resorbed in the body and permit a rapid growth of bone tissue into the thus-formed pores of the cement.

However, it is disadvantageous that special measures must be taken during processing to prevent the calcium phosphate particles from being saturated with monomeric acrylate or methacrylate. This is undesirable, because, thereby, the rapid, complete polymerization of the monomer is no longer ensured. There thus is the danger that a relatively large proportion of residual monomer will remain after curing and can pass into the patient's circulatory system. In addition, any monomer which polymerizes in the porous calcium phosphate particles will reduce the resorbability of the calcium phosphate thereby preventing formation of pores having the suitable dimensions.

These disadvantageous properties of the conventional, porous tricalcium phosphates, which can extensively prevent resorption, have not previously been recognized in the state of the art. They have especially not been recognized in the above-cited publication of J. Biomed. Mater. Res. This work describes implantation experiments and tests wherein only one filler is dissolved out of the cement, i.e., it uses only the very readily soluble and especially nonporous sucrose crystals.

Therefore, in an essential aspect of the present invention, there is made available a tricalcium phosphate which does not exhibit these disadvantageous properties. This object has likewise been attained by the present invention in a surprising fashion.

The absorption of liquid monomer into the porous calcium phosphate can be prevented if the pore volume of the calcium phosphate, prior to mixing it with the monomer, is filled with a physiologically compatible filler which is resorbable by the body and is immiscible with the monomer. Thereby, monomer is prevented from occupying the porous calcium phosphate. Suitable fillers of this type include, for example, glycerin, water, aqueous salt (e.g., sodium chloride or other physiologically acceptable salts or mixtures thereof) or physiologically acceptable buffer solutions, ethylene glycol, low-molecular weight polyethylene glycols, and lower alcohols, e.g., ethanol, n-propanol and isopropanol. Preferably, after this treatment, the available pore volume should be less than 0.1 ml/g.

To exclude these complications caused by the prior art porous structure of the calcium phosphate employed, it is, however, also possible to use a calcium phosphate having a very low porosity per se. The pore volume of these materials should be below 0.1 ml/g, preferably below 0.05 ml/g. These materials are obtained normally by sintering processes carried out at temperatures of around or above 1000° C. to approximately 1500° C. Precipitated, porous tricalcium phosphates can also be utilized as the starting materials in addition to the aforementiond compounds, e.g., CaO, $Ca(OH)_2$, $CaCO_3$, $CaHPO_4$ and $P_2O_5$. These originally relatively soft, porous materials discussed above increase markedly in hardness merely by an approximately one-hour-long heating at about 1200° C., preferably after previous compressing. At the same time, the pore volume is quite drastically reduced thereby to values lying well below 0.05 ml/g.

The same advantageous properties with regard to hardness and pore volume, however, can also be obtained by sintering other starting materials. Thus, for example, when sintering a mixture of calcium hydrogen phosphate and calcium carbonate at about 1200°-1500° C., there is also obtained a material having a pore volume almost at 0. The absorption of monomeric acrylate during processing need not be feared with these materials, so that a pretreatment of such calcium phosphates with the aforementioned fillers can be omitted.

The available pore volume of the resorbable tricalcium phosphate used in this invention is generally in the range of 0.0 to less than 0.1 ml/g and preferably is 0.0 to below 0.05 ml/g. The available pore volume referred to herein is that measured by the method of L. Gurwitsch, J. Phys. Chem. Soc. 47, 805 (1915).

The production of the tricalcium phosphates in the particle size required by this invention can be accomplished by methods known per se, for example, by grinding and screening. The particle size fraction of 50–300 μm according to this invention can, however, also be obtained by air separation or sedimentation treatments, for example. Particles having a size of 80–200 μm are especially preferred.

These tricalcium phosphate particles are incorporated into the bone cement in amounts of 5–35% by weight, preferably 15–30% by weight.

The conventional bone cements are prepared by mixing together about 2 parts of a finely divided prepolymer, especially polymethyl methacrylate or a copolymer of methyl acrylate and methyl methacrylate, containing a polymerization catalyst (e.g., dibenzoyl peroxide), with about one part of a liquid monomer, e.g., acrylic acid methyl ester or methacrylic acid methyl ester, or mixtures thereof, containing an accelerator (e.g., dimethyl p-toluidine), thereby forming a moldable composition, which latter is implanted in the body and cured therein. Such bone cements are commercially available, for example, under the name "Palacos". Such fully conventional bone cements are disclosed, for example, in U.S. Pat. Nos. 3,882,858 and 4,059,684, whose disclosures are incorporated by reference herein.

The implantation materials of this invention are produced, in an essentially similar manner. For example, the separate components, namely the prepolymer containing the polymerization catalyst; the tricalcium phosphate optionally pretreated with a filler; and the monomer containing the accelerator can be mixed together. However, it is also possible to prepare a premix of two of the three components by preparing a mixture of the tricalcium phosphate with either the prepolymer or with the monomer and then combining this mixture with the third component and uniformly mixing them together.

The prepolymers utilized according to the state of the art are generally without exception so-called bead polymers having a very smooth, uniform surface. Since no cross reaction takes place between the monomer and the prepolymer during the curing of the cement mixture, the prepolymer beads are merely enveloped by the newly forming polymer, but are not bound thereto. This can result in prepolymer beads, especially those lying in the marginal zones of the implant, which are not enveloped on all sides, and which can be relatively easily detached from the implant and flushed into the body where they can accumulate, for example, in lymph nodes.

Although the implantation materials of this invention yield very advantageous results even with these conventional bead polymers, and therefore the present invention includes these materials as well, it is preferred not to use beadshaped prepolymers, but rather to utilize prepolymers which, due to a more "angular" shape, cannot be detached from the subsequent bond so readily. Therefore, prepolymers are preferred which are present in the shape of irregular granules, flakes (flattened beads) or thread-like cylinders. The prepolymers should have a diameter of approximately 10–80 μm, preferably approximately 40–60 μm. The thread-shaped cylinders should not exceed a length of 1–2 mm.

If a porous tricalcium phosphate is employed and thus a pretreatment of the tricalcium phosphate with a filler is necessary, this pore filling can be effected in various ways. In any event, this filling of the pores should be conducted so that all pores are occupied, yet any amount of excess filler does not clog the tricalcium phosphate particles or subsequently have a negative influence on the curing of the implantation materials.

For relatively low-viscosity fillers, it is possible, for example, simply to add the stoichiometric or experimentally determined sufficient amount to the tricalcium phosphate, wherein, due to capillary forces, the filler is sucked into the pores. For higher-viscosity fillers, however, it is also possible to add the filler dissolved in a low-boiling solvent, to the tricalcium phosphate and then to evaporate the solvent. However, especially for relatively readily volatile fillers, it is also possible to fill the pores by vapor treatment. For this purpose, it is sufficient to bring the tricalcium phosphate, for example, in a closed system, in contact with the vapors formed above the liquid filler. Since the vapor pressure of the filler is lowered in the pores by capillary forces, a condensation of the filler takes place in the pores until the latter are completely occupied.

The most advantageous method depends on the particular filler employed. When using glycerin as the filler, for example, it proved to be advantageous to add the glycerin to the tricalcium phosphate while the former is dissolved in alcohol, and then to allow the alcohol to evaporate. The quantities in which the fillers must be utilized depend exclusively on the porosity of the tricalcium phosphate employed, since, as mentioned above, the pores must be filled to a maximally complete extent. However, it is preferred to employ a calcium phosphate which has such a low porosity that the filling of the pores can be avoided.

To avoid infections of the implant site, which cannot always be prevented even by careful aseptic manipulation, it is also possible to admix an antibiotic with the implantation material of this invention. In particular, an admixture of gentamycin is preferred, with which very good results are obtained. The use of gentamycin in bone cements is known per se, inter alia, from DOS No. 2,022,117. Yet, it is not obvious to admix gentamycin with the calcium-phosphate-containing bone cement of the present invention. For it has been known from "Antibiotik-Fibel" [Antibiotics Primer] 4th ed. (1975), bottom of page 373 to top of page 374, that gentamycin is reduced in efficacy by calcium salts, e.g., the phosphate.

However, it has surprisingly been found that even less gentamycin is necessary for incorporation into the calcium-phosphate-containing implantation materials of this invention than in the case of the conventional bone cements not containing calcium phosphate, to attain an identically high protection against infections of the implantation site. Although the amount of the antibiotic added can be varied within wide limits and thus can be completely adapted to the intended effect, the amounts of gentamycin to be incorporated into the materials of this invention to attain a specific effect are in all cases lower than the quantities required for conventional bone cements.

In conventional bone cements, additions of gentamycin of about 1–4% by weight have proved to be especially favorable. Since the release rate of gentamycin from the bone cement of this invention is surprisingly up to ten times higher than from the conventional bone cements containing gentamycin, this especially preferred range is, in case of the bone cements of this invention, about 0.1–2% by weight. Smaller and also larger additions of about 0.02 to 4% by weight can, however, be preferred for specific purposes.

In an antibiotic is to be mixed with the material of this invention, it is also possible to add other compounds, such as, for example, the amino acids known from DOS's Nos. 2,651,441 and 2,727,535, corresponding to U.S. application Ser. No. 845,703, filed on Oct. 26, 1977, now U.S. Pat. No. 4,191,740, whose disclosures are incorporated by reference herein, by means of which an especially uniform release of the antibiotic is attained. Of course, instead of gentamycin, other antibiotics can likewise be employed. Basically, all antibiotics are suitable which are not damaged by the temperatures occurring during polymerization, which are stable with respect to the synthetic resins employed and which are released in the desired way from the synthetic resin. From the large number of antibiotics which may be used, the following are set forth merely as examples: erythromycin, lincomycin, clindamycin, novobiocin, vancomycin, fusidic acid, rifampicin, polymycins, neomycin, kanamycin and tobramycin.

The mixing of the components can be accomplished in any suitable vessel, for example, in a dish or a beaker. Special mixing devices have likewise been proposed for this purpose. Due to the presence of the relatively heavy calcium phosphate, mixing must be conducted especially carefully to attain a homogeneous distribution of calcium phosphate in the implant. A special problem is the danger that air will be stirred into the composition which, especially in the form of air bubbles, will then be present in the cured implant as well. These can diminish the stability of the implant. Especially also due to the poor wettability of the calcium phosphate surface with respect to the liquid monomer, air bubbles accumulate particularly on the calcium phosphate particles, preventing the contact of calcium phosphate and cement, thereby considerably diminishing the stability of the cured implant. An examination of the conventional bone cements has shown, furthermore, that air bubbles of diameters normally of 50–200 $\mu$m, likewise arise around the polymer beads as a consequence of flow effects. This volume proportion of occluded air bubbles can represent up to 15 percent by volume in the finished cement.

These air bubble occlusions, which can be observed in the implants of this invention with the addition of calcium phosphate, as well as in the prior-art implants, can be reduced surprisingly by a process step relatively simple to execute, at least to such an extent that the stability of the implants is considerably increased. For it has been found that a compression of the mixture of tricalcium phosphate, prepolymer and monomer, or also of the mixture of only prepolymer and monomer, in a specific phase of the polymerization, extensively inhibits the formation of air occlusions. This compression step is to occur in the first period of the processing phase of the bone cements and directly follows the mixing of prepolymer and monomer or the mixing of tricalcium phosphate, prepolymer and monomer. For example, implantation materials of such a composition that they are cured after about 6–15 minutes after mixing and are processable approximately up to the 2nd to 8th minute after mixing, are preferably exposed to an increased pressure in the time between the 1st and 4th minute. The timing of the compression treatment for other compositions will be more or less proportional and can be readily determined by routine experiments.

The compression is preferably performed so that the mixture of tricalcium phosphate, prepolymer, and monomer is compressed in a plunger-type syringe of a suitable size, provided with venting holes, the width of these holes preventing the penetration of the viscous mixture but permitting trapped air to escape, wherein the plunger of this syringe is not sealed off airtight with respect to the syringe wall. The pressures required for this purpose can be produced by an internal thread of the syringe using only moderate force, so that it is possible, for example, even for physically weaker operating personnel, e.g., some females, to easily generate the pressures according to this invention of 10–45 kp/cm$^2$, preferably 20–40 kp/cm$^2$. The pressure is maintained for a limited period of time, preferably for about 1–2 minutes, the suitable period being readily determined for a particular material by routine experiments. After removal of the narrow hollow outlet needle serving as the venting hole, the implantation material can be forced out of the syringe through a sufficiently wide outlet cannula and introduced into the body.

Implantation materials with or without calcium phosphate produced with such a precompression treatment exhibit a very greatly reduced proportion of air occlusions, wherein these few occlusions have only a very small diameter. It is striking in the implantation materials containing calcium phosphate per this invention that, for specimens produced with this precompression, a solid bond of the polymer to the calcium phosphate is established, which is not disturbed by air occlusions on the calcium phosphate surface. Materials manufactured with precompression thus exhibit a considerably higher strength than those directly introduced into the body after mixing. The processing of the materials of this invention with precompression is, therefore, another essential aspect of the present invention.

Another particular advantage displayed by the bone cements of this invention is represented by the fact that the mixing of an X-ray constrast medium can be eliminated. Normally, barium sulphate is mixed with the customary bone cements as such an X-ray contrast medium, but this compound causes relatively grave problems due to its toxicity. The calcium phosphate contained in the bone cements of this invention, however, itself provides sufficiently effective X-ray absorption so that no additional X-ray contrast medium needs to be added.

The implantation materials of this invention, especially those produced according to the precompression process of this invention, can be utilized to very great advantage in the combating of bone defects and in other conventional uses of bone cements. They can serve, on the one hand, for the implantation of endoprostheses, but on the other hand, also for conducting so-called composite osteosyntheses and for the filling in of certain bone defects.

In accordance with the foregoing, it can be seen that the implantation material of this invention can be conveniently prepared by admixing the contents of a container of (a) 8–10 wt. parts of a composition containing, inter alia, 10–50 wt.% of the resorbable tricalcium phosphate of this invention and 50–90 wt.% of the prepolymer, with (b) the contents of a container of, inter alia, 2–4 wt. parts of the liquid monomer component; or admixing the contents of a container of (a) 5–8 wt. parts of a composition containing, inter alia, 10–60 wt.% of the resorbable tricalcium phosphate of this invention and 40–90 wt.% of the liquid monomer, with (b) the contents of a container of, inter alia, 4–9 wt. parts of the prepolymer.

Without further elaboration, it is believed that one skilled in the art can, using the preceding description, utilize the present invention to its fullest extent.

The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

40 g. of a precipitated tricalcium phosphate of the chemical formula $Ca_5(PO_4)_3OH$ having a pore volume of 0.4 ml./g. is combined with 20 ml. of glycerin in 50 ml. of absolute alcohol and allowed to stand in a desiccator for 24 hours to remove the alcohol. A quantity of 5 g. of this pretreated tricalcium phosphate, having an average particle size of between 100 and 200 μm., is thoroughly mixed with 5.5 ml. of the methyl ester of methacrylic acid, containing 0.7% dimethyl p-toluidine and about 0.006% hydroquinone (called "monomer" hereinbelow) and 10.0 g. of a finely divided copolymer of the methyl esters of acrylic acid and methacrylic acid (particle diameter <30 μm.), containing 0.5% dibenzoyl peroxide and traces of chlorophyll (called "polymer" hereinbelow).

The composition is compressed from the 1st to the 3rd minute after mixing with a pressure of about 35 kp./cm² and can be processed within the first three to six minutes, is still plastically deformable up to about the eighth minute, and is solid after about 10–11 minutes. The thus-obtained cement is well hardened and shows no residues of glycerin on the surface. Similarly good results are obtained with the use of 7 ml. of monomer and especially when using 6 ml. of monomer.

EXAMPLE 2

40 g. of the precipitated tricalcium phosphate of Example 1 is combined with 30 ml. of glycerin in 40 ml. of absolute alcohol and allowed to stand for 24 hours in a desiccator to remove the alcohol. A quantity of 5 g. of this tricalcium phosphate, treated as described, is thoroughly mixed with 6 ml. of monomer and 10 g. of polymer. The composition can be mixed very readily and can be extruded from the 2nd to the 9th minute, can be kneaded by hand up to the 11th minute, is warm after about 12 minutes, and is cured after about 13 minutes. The thus-obtained cement is of very satisfactory hardness and the surface is free of glycerin residues. Compression to a pressure of about 35 kp./cm² takes place between the 1st and 3rd minutes.

EXAMPLE 3a

The following starting materials
A a precipitated tricalcium phosphate having a pore volume of 0.35 ml./g. (E. Merck, article No. 2143),
B a precipitated tricalcium phosphate having a pore volume of 0.40 ml./g.,
C an intimate mixture of 2 parts of calcium hydrogen phosphate and one part of calcium carbonate
are preliminarily granulated in an eccentric press and then compressed into pellets.

The starting materials A and B are then annealed for respectively one hour at 600°; 900°; 1200°; and 1500° C. and starting material C is initially annealed for 3 hours at 1200° C., then coarsely divided, again compressed into pellets, and annealed for one hour at 1500° C.

The following table shows the specific surface areas and specific pore volumes of the thus-treated starting materials.

| Material | Temperature (°C.) | Specific Surface Area (cm²/g.) | Specific Pore Volume (ml./g.) |
|---|---|---|---|
| A |  | 50.8 | 0.35 |
| A | 600 | 27.8 | 0.30 |
| A | 900 | 10.4 | 0.29 |
| A | 1200 | 3.4 | 0.02 |
| A | 1500 | 0.8 | 0.01 |
| B |  | 73.2 | 0.40 |
| B | 600 | 20.9 | 0.30 |
| B | 900 | 6.0 | 0.04 |
| B | 1200 | 2.0 | 0.01 |
| B | 1500 | 0.6 | 0.01 |
| C | 1200 | 2.1 | 0.01 |
| C | 1500 | 1.1 | 0.01 |

A crystallographic examination of the materials shows that A and B, at all annealing temperatures, exhibit a hydroxylapatite structure whereas C exhibits a whitlockite structure.

The annealed materials can be obtained in all desired particle sizes by comminution and classification.

EXAMPLE 3b 5 g. of the tricalcium phosphate A annealed at 1200° C. according to Example 3a, having a particle size of between 63 and 200 μm. is thoroughly mixed with 6 ml. of monomer and 10 g. of polymer. From about the first to about the third minute, the mixture is compressed under a pressure of about 35 kp./cm². The composition can be extruded up to the fifth minute, can be kneaded by hand and is plastically deformable up to the eighth minute, is warm after about 9 minutes, and is cured after about 10 minutes. The thus-obtained bone cement is of satisfactory hardness.

Materials B and C, annealed at 1200°–1500° C., can also be utilized in the same way and with equally good results.

EXAMPLE 4

20 g. of the tricalcium phosphate A annealed at 1200° C. according to Example 3a, having a particle size of between 50 and 300 μm., is thoroughly mixed with 24 ml. of monomer and 40 g. of polymer. From about the first to the third minute, the mixture is compressed in a plunger-type syringe under a pressure of about 35 kp./cm².

A hip joint, deformed by arthritis, is opened up; the neck of the femur is prepared so that it is uncovered, the capsule is removed, and the head of the femur with the neck of the femur is resected 1 cm. above the trochanter minor in an angle to the horizontal plane of 35°–45°; the medullary cavity is curetted and prepared with a special bur so that an artificial metal prosthesis can be fitted. A venting hose is introduced into the thus-prepared femur marrow cavity, this hose extending to underneath the tip of the prosthesis.

The bone cement composition, prepared in the abovedescribed way, is then injected into the flushed-out medullary cavity prepared in the above manner; subsequently, the metal shank prosthesis is introduced in such a way that the metal shank is entirely surrounded by bone cement and does not perforate this synthetic resin sheath anywhere. This is attained by planning the angle of implantation and the resection surfaces by preoperative drawings, whereby the location where the metal prosthesis enters the plastic cement can be predetermined. In this position, the thus-implanted metal prosthesis is retained immovably up to the eleventh minute under pressure. After this time period, the bone cement has hardened, and the prosthesis is implanted in a stable fashion.

The shrinkage fissures occurring in the boundary zone are so small that, with normal bone vascularization, the fissure is filled in with bone after at most 12 weeks, so that the artificial prosthesis can be placed under full load starting with this point in time.

EXAMPLE 5

An arthritic femur head, which, however, is still well preserved in its external shape, can also be prepared for a so-called cap prosthesis. For this purpose, the femur head is freed of its residual cartilage. The basic cartilaginous plate is prepared with a special bur so that bleeding centers of ossification become visible. The hip cap is fitted in such a way that the boundary zone of bone and cement is primarily under compressive stress, i.e. in opposition to the physiological angular position of the femur head, the cap is placed in valgus and in a deflected fashion onto the head of the femur.

Subsequently the head of the femur is dried, and the cap prosthesis is coated with a 2 mm. thick layer of a cement prepared in the way described in Example 4. The cap containing the cement is then inverted over the thoroughly dry head of the femur and firmly pressed thereagainst. The thus-escaping cement is removed, and the cap is held under pressure in the carefully planned position up to the eleventh minute. The thus-fixed metal cap immediately exhibits a sufficiently stable seat so that the capped femur head can be replaced without difficulties into the artificial acetabulum implanted into the pelvis.

EXAMPLE 6

In cases of bone fractures, especially so-called pathological fractures in case of bone tumors or bone metastases of other primary tumors, a composite osteosynthesis can be utilized. In this connection, two fragments wherein metallic screws can no longer be securely fastened into place are filled in from the medullary cavity with a bone cement prepared according to EXAMPLE 4 in such a way that it is possible to affix a metal plate with screws either directly into the soft cement or, after drilling and cutting a thread into the cured cement, onto this bond of bone and bone cement.

Such a composite osteosynthesis can also be executed by reinforcing the composite of cement and bone by means of an intramedullary metal nail which, so to speak, threads the fragments into position. After curing of the cement, the screws or metallic implants attain a firm hold, so that rapid bone healing can be effected. It could be shown that healing of the bone is not interfered with by the cement filling.

EXAMPLE 7

In certain cases wherein bone tumors have occurred in the close proximity of the epiphysis, large bone defects wherein a replenishment by the body's own ossification can no longer be expected and on the basis of which the extremity can no longer be safely placed under stress, can be filled up with bone cements, and the extremities, with or without metallic reinforcement, can be filled up with the bone cement prepared according to Example 4. The thus-treated bones regain a load stability or at least an exercising stability contributing to a considerable facilitation of nursing care.

EXAMPLES 8–10

Examples 1–3 are repeated, wherein instead of the finely divided prepolymer used therein, a granulated polymer is employed having a particle size of 40–60 $\mu$m.

EXAMPLES 11–13

Examples 1–3 are repeated, wherein instead of the finely divided prepolymer used therein, thread-like polymer cylinders are utilized having a length of 0.5–1 mm. and a diameter of about 50 $\mu$m.

EXAMPLE 14

A bone cement mixture is prepared from 30 g. of polymer, 21 ml. of monomer, 15 g. of tricalcium phosphate, and 0.5 g. of gentamycin base; from this bone cement mixture, cylindrical test bodies are formed having a diameter of 25 mm. and a height of 10 mm. Such a test body is introduced into 20 ml. of a phosphate buffer, pH 7.4. After respectively 24 hours, the liquid is changed and examined for its gentamycin content. For comparison purposes, an analogous test body is utilized formed from a mixture of 40 g. of polymer, 20 ml. of monomer, and 0.5 g. of gentamycin base.

The comparison brought the following result:

| | Gentamycin Content in the Liquid ($\mu$g./ml.) | |
|---|---|---|
| | Conventional Bone Cement | Bone Cement of Invention |
| 1st Day | 83 | 260 |
| 2nd Day | 12 | 119 |
| 3rd Day | 5.6 | 67 |
| 4th Day | 4.5 | 52 |
| 5th Day | 3.8 | 38 |

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An implantation material comprising a polymeric base of a polyacrylate, a polymethacrylate, a copolymer of an acrylate and a methacrylate or a mixture thereof and 5–35% by weight of resorbable tricalcium phosphate of a particle size of 50–300 $\mu$m and an available pore volume of less than 0.1 ml/g.

2. The material of claim 1, further comprising a pharmacologically active agent.

3. The material of claim 2, wherein the active agent is an antibiotic.

4. The material of claim 2, wherein gentamycin is the active agent.

5. The material of claim 1, wherein the resorbable tricalcium phosphate has been prepared by sintering calcium-containing and phosphorus-containing compounds which directly produces a resorbable tricalcium phosphate having an available pore volume of less than 0.1 ml/g.

6. The material of claim 1, wherein the resorbable tricalcium phosphate has been prepared by impregnating the pores of a tricalcium phosphate of an available pore volume greater than 0.1 ml/g with a resorbable physiologically compatible filler such that the available pore volume is decreased to less than 0.1 ml/g.

7. The material of claim 1, which is formed by mixing particles of a prepolymer of the polymeric base, a polymerization catalyst, a liquid acrylic or methacrylic monomer and the resorbable tricalcium phosphate.

8. The material of claim 7, wherein the particles of prepolymer have a diameter of approximately 10-80 μm.

9. The material of claim 8, wherein the particles of prepolymer are irregular granules, flakes or thread-like cylinders of a length of 0.1-2 mm.

10. A method of preparing an implantation material having a polymeric base of a polyacrylate, a polymethacrylate, a copolymer of an acrylate and a methacrylate or a mixture thereof comprising preparing the implantation material in its moldable stage and, prior to the curing thereof, compressing the moldable implantation material thereby removing occluded air therefrom, wherein the implantation material is that of claim 7.

11. The process of claim 10, wherein the implantation material is compressed under a pressure of approximately 10-45 kp/cm$^2$.

12. A composition for use in preparing an implantation material comprising 10-50 wt.% of resorbable tricalcium phosphate of a particle size of 50-300 μm and an available pore volume of less than 0.1 ml/g and 50-90 wt.% of prepolymer particles of a polyacrylate, a polymethacrylate, a copolymer of an acrylate and a methacrylate or a mixture thereof.

13. A composition for use in preparing an implantation material comprising 10-60 wt.% of resorbable tricalcium phosphate of a particle size of 50-300 μm with an available pore volume of less than 0.1 ml/g and 40-90 wt.% of an acrylic or methacrylic monomer.

14. A kit for preparing an implantation material comprising a container of 8-10 wt. parts of the composition of claim 12 and a container of 2-4 wt. parts of an acrylic or methacrylic monomer.

15. A kit for preparing an implantation material comprising a container of 5-8 wt. parts of the composition of claim 13 and a container of 4-9 wt. parts of prepolymer particles of a polyacrylate, a polymethacrylate, a copolymer of an acrylate and a methacrylate or a mixture thereof.

16. A method of treating bone defects requiring implantation of a bone cement in a bone of a patient, comprising implanting the implantation material of claim 1 in a bone of the patient.

17. An implantation material of claim 1 wherein the available pore volume of the resorbable tricalcium phosphate is less than 0.05 ml/g.

* * * * *